US010222383B2

(12) United States Patent
Campbell et al.

(10) Patent No.: US 10,222,383 B2
(45) Date of Patent: Mar. 5, 2019

(54) METHODS AND COMPOSITIONS FOR DETECTING MYCOPLASMA EXPOSURE

(71) Applicant: Advanced Animal Diagnostics, Inc., Morrisville, NC (US)

(72) Inventors: Robert L. Campbell, Bullock, NC (US); Melissa E. Langer, Morrisville, NC (US); Jasper N. Pollard, Durham, NC (US); Robert L. Cheek, Mebane, NC (US); Kevin G. Dolan, Holly Springs, NC (US); W. William Stewart, Cary, NC (US); Stefano Bresolin, Garner, NC (US); John Richard Sink, Raleigh, NC (US); Tobias M. Heineck, Durham, NC (US); Laura A. Black, Holly Springs, NC (US); Nathan F. Pope, Raleigh, NC (US); Lauren K. Parker, Edenton, NC (US); Erik J. Jensen, Hillsborough, NC (US); Jorge Carlos Correa, Raleigh, NC (US); Reha O. Azizoglu, Morrisville, NC (US)

(73) Assignee: Advanced Animal Diagnostics, Inc., Morrisville, NC (US)

( * ) Notice: Subject to any disclaimer, the term of this patent is extended or adjusted under 35 U.S.C. 154(b) by 0 days.

(21) Appl. No.: 15/418,477

(22) Filed: Jan. 27, 2017

(65) Prior Publication Data
US 2017/0219604 A1 Aug. 3, 2017

Related U.S. Application Data

(60) Provisional application No. 62/375,584, filed on Aug. 16, 2016, provisional application No. 62/288,872, filed on Jan. 29, 2016.

(51) Int. Cl.
*G01N 33/68* (2006.01)
*G01N 33/558* (2006.01)
*G01N 33/569* (2006.01)

(52) U.S. Cl.
CPC ....... *G01N 33/6854* (2013.01); *G01N 33/558* (2013.01); *G01N 33/56933* (2013.01); *G01N 2333/30* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 4,998,284 A | 3/1991 | Bacus et al. | |
| 5,571,667 A | 11/1996 | Chu et al. | |
| 5,673,647 A | 10/1997 | Pratt | |
| 5,790,710 A | 8/1998 | Price et al. | |
| 5,798,273 A | 8/1998 | Shuler et al. | |
| 5,939,326 A | 8/1999 | Chupp et al. | |
| 6,004,512 A | 12/1999 | Titcomb et al. | |
| 6,350,613 B1 | 2/2002 | Wardlaw et al. | |
| 6,381,058 B2 | 4/2002 | Ramm et al. | |
| 6,617,116 B2 | 9/2003 | Guan et al. | |
| 6,720,160 B2 | 4/2004 | Wolde-Mariam | |
| 6,927,903 B2 | 8/2005 | Stuckey | |
| 6,929,953 B1 | 8/2005 | Wardlaw | |
| 7,270,995 B2 | 9/2007 | Matsushita et al. | |
| 7,879,597 B2 | 2/2011 | Esfandiari | |
| 8,000,511 B2 | 8/2011 | Perz | |
| 8,045,165 B2 | 10/2011 | Wardlaw et al. | |
| 8,081,303 B2 | 12/2011 | Levine et al. | |
| 8,418,660 B2 | 4/2013 | Huls | |
| 8,877,450 B2 | 11/2014 | Esfandiari | |
| 2001/0041347 A1 | 11/2001 | Sammak et al. | |
| 2003/0099929 A1 | 5/2003 | Vojdani | |
| 2004/0023404 A1 | 2/2004 | Shibata | |
| 2004/0170601 A1 | 9/2004 | Strom et al. | |
| 2006/0166366 A1 | 7/2006 | Matsumoto et al. | |
| 2009/0233329 A1 | 9/2009 | Rodriguez et al. | |
| 2011/0306511 A1 | 12/2011 | Lea | |
| 2013/0222895 A1 | 8/2013 | Gelbart | |
| 2014/0009596 A1 | 1/2014 | Bresolin et al. | |
| 2014/0186394 A1 | 7/2014 | Jordan et al. | |

FOREIGN PATENT DOCUMENTS

| | | |
|---|---|---|
| DE | 198 33 636 C1 | 5/2000 |
| WO | WO 02/056017 A1 | 7/2002 |
| WO | WO 2007/027231 A1 | 3/2007 |
| WO | WO 2008/021862 A2 | 2/2008 |
| WO | WO 2008/039171 A2 | 4/2008 |
| WO | WO 2015/042571 A1 | 3/2015 |
| WO | WO 2017/019743 A1 | 2/2017 |

OTHER PUBLICATIONS

Schutz-Geschwender et al. p. 1-8. May 2004. LI-COR Biosciences. Retrieved Jun. 29, 2018 from https://www.licor.com/bio/PDF/IRquant.pdf.*
Eterpi et al. "Decontamination efficacy against *Mycoplasma*" *Letters in Applied Microbiology* 52:150-155 (2010).
International Search Report and the Written Opinion of the International Searching Authority corresponding to International Patent Application No. PCT/US2017/015453 (16 pages) (dated May 31, 2017).
International Search Report and the Written Opinion of the International Searching Authority corresponding to International Patent Application No. PCT/US2017/023675 (17 pages) (dated Jun. 16, 2017).
Mayo Clinic "*Mycoplasma pneumoniae* Antibodies, IgG and IgM, Serum" *Test ID: MYCPN* (3 pages) (Jun. 10, 2013).
Meridian Healthcare "Immunoflow" *Mycoplasma pneumoniae* IgM *Test* (4 pages) (Jun. 1, 2014).
Qscout Farm Lab Product Brochure www.qscoutlab.com (2 pages) (Dec. 24, 2014).
Ruegg et al. "Milk Quality and Mastitis Tests" *University of Wisconsin* (34 pages) (2002).
Stilwell et al. "The Effect of Duration of Manual Restraint During Blood Sampling on Plasma Cortisol Levels in Calves" *Animal Welfare* 17:383-385 (2008).
International Preliminary Report on Patentability corresponding to International Patent Application No. PCT/US2017/015453 (13 pages) (dated Jul. 31, 2018).

\* cited by examiner

*Primary Examiner* — Oluwatosin A Ogunbiyi
(74) *Attorney, Agent, or Firm* — Myers Bigel, P.A.

(57) ABSTRACT

The present invention provides methods and compositions for detecting *Mycoplasma* exposure in a subject.

34 Claims, 8 Drawing Sheets

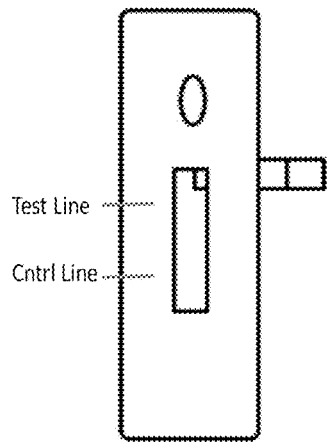
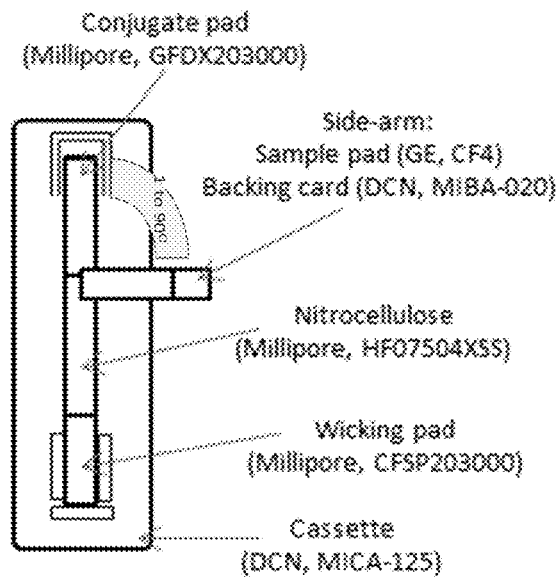
FIG. 3A: Outside view of assembled cassette
FIG. 3B: Inside view of assembled cassette
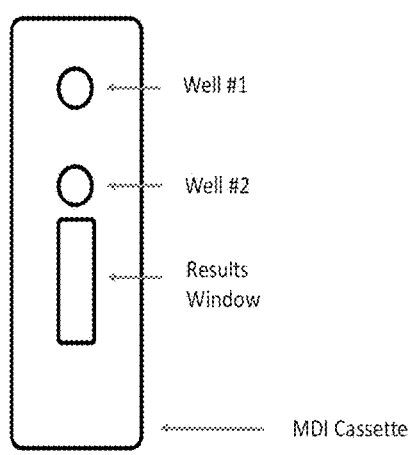
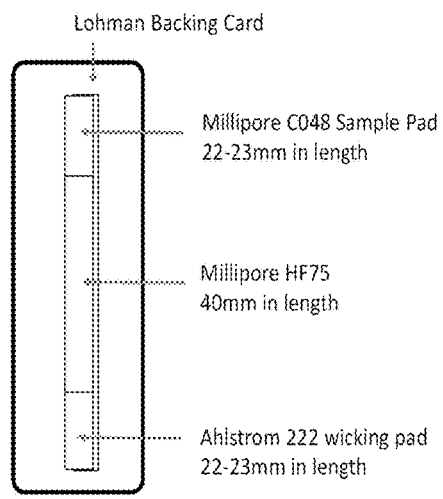
FIG. 4A: Outside view of assembled cassette
FIG. 4B: Inside view of assembled cassette

METHODS AND COMPOSITIONS FOR DETECTING MYCOPLASMA EXPOSURE

STATEMENT OF PRIORITY

This application claims the benefit, under 35 U.S.C. § 119(e), of U.S. Provisional Application Ser. No. 62/288,872, filed Jan. 29, 2016 and U.S. Provisional Application Ser. No. 62/375,584, filed Aug. 16, 2016, the entire contents of each of which are incorporated by reference herein.

FIELD OF THE INVENTION

The present invention concerns methods and apparatus for detecting analytes, including pathogens such as *Mycoplasma* species, in liquid samples such as biological fluids, including milk, colostrum, blood and serum.

BACKGROUND OF THE INVENTION

The *Mycoplasma* are a wide-spread group of bacteria. Species such as *M. pneumoniae,* and *M. genitalium* cause disease in humans. Related species cause disease in plants. *M. bovis* is considered one of the more pathogenic species and causes pneumonia, mastitis and arthritis in cattle. In research laboratories, *Mycoplasma* species are frequent contaminants in cell cultures.

*Mycoplasma* are characterized by the absence of a cell wall. Unfortunately, the most important group of antibiotics, the beta lactams, (which include both the penicillins and the cephalosporins) function by inhibiting cell wall synthesis. With important antibiotics such as these unavailable for the treatment of mycoplasma infections, there is a need for new and rapid methods and apparatus for the detection of these species so that they may be quickly detected on occurrence and controlled or eradicated before the spread thereof. In summary, *Mycoplasma* and particularly *M. bovis* is a substantial threat to dairies and an unaddressed. *Mycoplasma* infection can lead to business foreclosure.

Major deficiencies exist today with the mycoplasma diagnostic tests available to dairymen. For example, none of the current tests can provide dairymen with an immediate (e.g., within 20 minute—while the cows are still in the milking parlor) ability to discriminate, among cows that have been exposed to mycoplasma, those that are suffering with an infection from those cows who have not come in contact with mycoplasma. Current culture tests take up to 10 days and cannot discriminate antibiotic resistant mycoplasma from the closely related *Acholeplasma* that has identical agar plate morphology, but is treatable with antibiotics. Another problem with current culture methods is that these tests cannot be performed on a milk sample containing mycoplasma that has been frozen. Freezing reduces the ability of mycoplasma to grow on agar plates. Further, since animals that are positive for mycoplasma only shed organism intermittently, many tests for antigen, either viable intact organism or organism fragments, will frequently suggest an animal is negative for mycoplasma when indeed the animal has a current infection.

In summary, the industry needs a test that can provide results in 20 minutes or less, a test that can be performed on frozen milk samples, and a test system that can discriminate *M. bovis* from *Acholeplasma.* The test must also be able to discriminate animals that have been exposed and those with a current or recent infection, and include detecting those mycoplasma positive animals that are intermittently shedding live organism. Furthermore, the industry needs some combination of rapid tests that work directly and indirectly by different mechanisms, which used together provide reliable evidence that an animal is positive for mycoplasma. In particular embodiments, some combination of tests that probe for antigen and the cow's immune response would be ideal for confirming infection.

The present invention overcomes previous shortcomings in the art by providing methods and compositions for the rapid detection of mycoplasma infection in animals.

SUMMARY OF THE INVENTION

The present invention provides a method of detecting *Mycoplasma* exposure in a subject, comprising: (a) providing an aqueous sample comprising a biological fluid from the subject; (b) contacting said aqueous sample to at least one solid support, each said at least one support having a mycoplasma antigen immobilized thereon, under conditions wherein an antigen/antibody complex will form if said aqueous sample contains an antibody to *Mycoplasma;* (c) contacting an anti-IgG antibody coupled to a first detectable group with said aqueous sample of step (b) on said solid support, under conditions wherein an antibody/antibody complex will form if said aqueous sample contains an antibody to *Mycoplasma;* (d) detecting the presence or absence of said first detectable group on said at least one solid support; (e) contacting an anti-IgM antibody coupled to a second detectable group, with said aqueous sample of step (b) on said solid support, under conditions wherein an antibody/antibody complex will form is said aqueous sample contains an antibody to *Mycoplasma;* and detecting the presence or absence of said second detectable group on said at least one solid support, wherein detection of the presence of said first detectable group and/or of said second detectable group on said solid support detects *Mycoplasma* exposure in said subject.

In some embodiments, the method can further comprise the steps of: (g) quantitatively determining the amount of anti-*Mycoplasma* IgG antibodies and the amount of anti-*Mycoplasma* IgM antibodies in said biological fluid; (h) calculating a value X by assigning a relative intensity value to the amount of anti-*Mycoplasma* IgG antibodies and a value Y by assigning a relative intensity value to the amount of anti-*Mycoplasma* IgM antibodies; (i) calculating a value Z by adding X and Y of step (h); and (j) identifying the subject as having Zone 1, Zone 2 of Zone 3 status regarding *Mycoplasma* exposure, wherein Zone 1 status is identified when Z is a high relative intensity value and indicates an active infection or recent exposure to mycoplasma, Zone 2 is identified when Z is a medium relative intensity value and indicates a prior exposure to mycoplasma, and Zone 3 is identified when Z is a low relative intensity value and indicates no prior exposure to mycoplasma.

In some embodiments, the method of this invention can further comprise the steps of (g) quantitatively determining the amount of anti-*Mycoplasma* IgG antibodies and the amount of anti-*Mycoplasma* IgM antibodies in said biological fluid using a QSCOUT™ signal reader instrument; (h) calculating a value X using the QSCOUT™ signal reader instrument; and (i) identifying the subject as having Zone 1, Zone 2 or Zone 3 status regarding *Mycoplasma* exposure, wherein Zone 1 status is identified when X is equal to or greater than 16 and indicates an active infection or recent exposure to mycoplasma, Zone 2 is identified when X is between 6 and 16 and indicates a prior exposure to mycoplasma, and Zone 3 is identified when X is equal to or less than 6 and indicates no prior exposure to mycoplasma.

Additionally provided herein is a composition, comprising: (a) an antigen, said antigen comprising whole *Mycoplasma* inactivated with hydrogen peroxide; and (b) an absorbent support to which said antigen is coupled. In some embodiments, the composition can further comprise (c) a cassette housing in which said absorbent support is contained.

Further provided herein is an apparatus for determining *Mycoplasma* exposure in a subject, the apparatus comprising: an imaging reader configured to image a sample having an anti-*Mycoplasma* IgG antibody intensity signal and an anti-*Mycoplasma* IgM antibody intensity signal; and a controller configured to (a) receive the anti-*Mycoplasma* IgG antibody intensity signal and the anti-*Mycoplasma* IgM antibody intensity signal from the image reader; (b) calculate a value X by assigning a relative intensity value to the anti-*Mycoplasma* IgG antibody intensity signal and a value Y by and an anti-*Mycoplasma* IgM antibody intensity signal; (c) calculate a value Z by adding X and Y of step (b); and (d) identify the subject as having a Zone 1, Zone 2 or Zone 3 status regarding *Mycoplasma* exposure, wherein Zone 1 status is identified when Z is a high relative intensity value and indicates an active infection or recent exposure to mycoplasma; Zone 2 status is identified when Z is a medium relative intensity value and indicates a prior exposure to mycoplasma; Zone 3 is identified when Z is a low relative intensity value and indicates no prior exposure to mycoplasma.

The method of this invention may be carried out sequentially or simultaneously, with separate cartridges/supports or combination cartridges/supports, and in any suitable format, including but not limited to lateral flow, dipstick, and flow-through formats.

The method shows good distinction between *Mycoplasma bovis* and *Acheloplasma*.

In some embodiments, the method is suitable for use "on farm" or in other rugged outdoor environments, or in other conditions where a simple and rapid screening procedure is desired.

The foregoing and other objects and aspects of the present invention are explained in greater detail in the drawings herein and the specification set forth below.

BRIEF DESCRIPTION OF THE DRAWINGS

FIG. 3A. Exterior schematic illustration of a side-arm lateral flow assay cartridge (side arm angled 1-90 degrees from main backer card). The side-arm is typically removed after specimen addition, and not present during test line signal generation. The side-arm may be in contact with the nitrocellulose, the conjugate pad, or both.

FIG. 3B. Interior schematic illustration of the side-arm lateral flow assay cartridge of FIG. 3A.

FIG. 4A. Exterior schematic illustration of a two-hole lateral flow assay cartridge (no side-arm required).

FIG. 4B. Interior schematic illustration of the two-hole lateral flow assay cartridge of FIG. 4A.

DETAILED DESCRIPTION OF THE INVENTION

Figure 1:
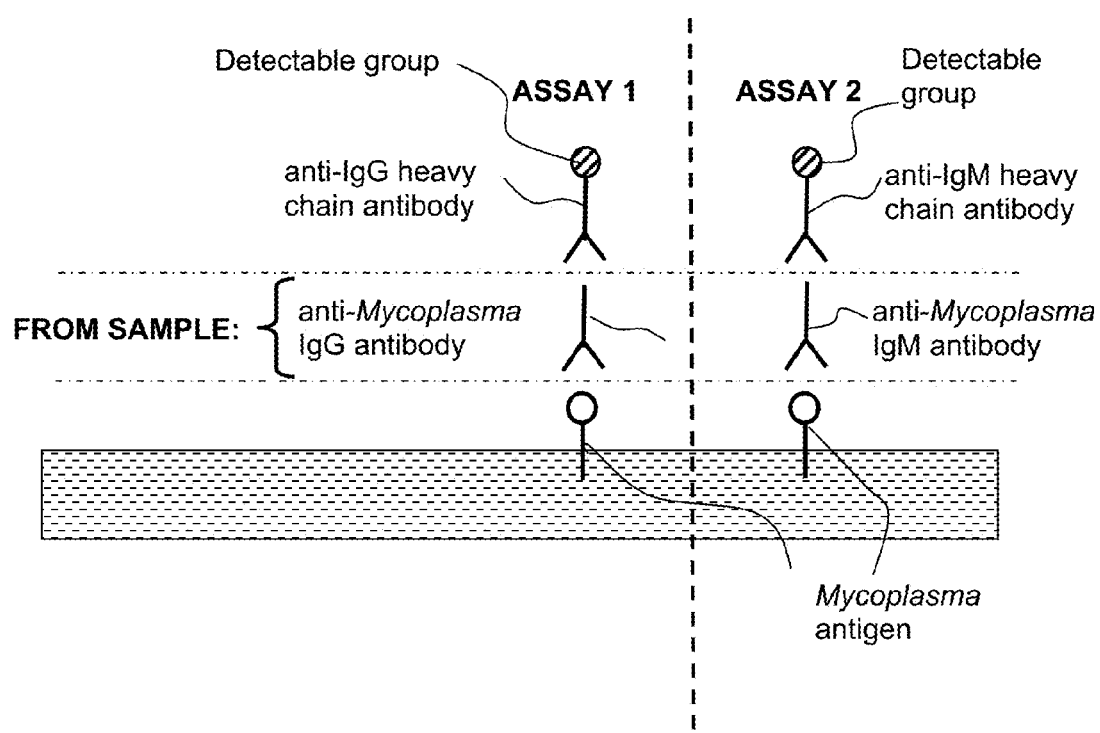
FIG. 1. Schematic illustration of an assay system according to some aspects of the invention.

The present invention now will be described more fully hereinafter with reference to the accompanying figures, in which embodiments of the invention are shown. This invention may, however, be embodied in many alternate forms and should not be construed as limited to the embodiments set forth herein. Rather, these embodiments are provided so that this disclosure will be thorough and complete, and will fully convey the scope of the invention to those skilled in the art. Like numbers refer to like elements throughout the description of the figures.

The terminology used in the description of the invention herein is for the purpose of describing particular embodiments only and is not intended to be limiting of the invention.

A subject "in need thereof" as used herein refers to a subject that can benefit from the therapeutic and/or prophylactic effects of the pharmaceutical compositions of the present invention. Such a subject can be a subject diagnosed with a disease or disorder of this invention, a subject suspected of having or developing a disorder or disease of this invention, and/or a subject determined to be at increased risk of having or developing a disease or disorder of this invention.

By the term "treat," "treating," or "treatment of" (and grammatical variations thereof) it is meant that the severity of the subject's condition is reduced, at least partially improved or ameliorated, and/or that some alleviation, mitigation or decrease in at least one clinical symptom is achieved and/or there is a delay in the progression of the disease or disorder.

The terms "prevent," "preventing," and "prevention of" (and grammatical variations thereof) refer to reduction and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of a composition of the present invention.

As used herein, the terms "therapeutically effective amount" or "effective amount" refer to an amount of a composition or formulation of this invention that elicits a therapeutically useful response in a subject. Those skilled in the art will appreciate that the therapeutic effects need not be complete or curative, as long as some benefit is provided to the subject.

As used in the description of the invention and the appended claims, the singular forms "a," "an" and "the" are intended to include the plural forms as well, unless the context clearly indicates otherwise. For example, "a cell" can mean a single cell or a multiplicity of cells.

Also as used herein, "and/or" refers to and encompasses any and all possible combinations of one or more of the associated listed items, as well as the lack of combinations when interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP §2111.03. Thus, the term "consisting essentially of" as used herein should not be interpreted as equivalent to "comprising."

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein the term "and/or" includes any and all combinations of one or more of the associated listed items.

The term "about," as used herein when referring to a measurable value such as an amount or concentration (e.g., the amount of the benzodiazepine in the pharmaceutical composition) and the like, is meant to encompass variations of 20%, 10%, 5%, 1%, 0.5%, or even 0.1% of the specified amount.

Unless the context indicates otherwise, it is specifically intended that the various features of the invention described herein can be used in any combination. For example, features described in relation to one embodiment may also be applicable to and combinable with other embodiments and aspects of the invention.

Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular embodiments only and is not intended to be limiting of the invention. All publications, patent applications, patents and other non-patent references mentioned herein are incorporated by reference in their entirety.

In one aspect, the present invention provides a method of detecting *Mycoplasma* exposure in a subject, comprising: (a) providing an aqueous sample comprising a biological fluid from the subject; (b) contacting said aqueous sample to at least one solid support, each said at least one support having a mycoplasma antigen immobilized thereon, under conditions wherein an antigen/antibody complex will form if said aqueous sample contains an antibody to *Mycoplasma*; (c) contacting an anti-IgG antibody coupled to a first detectable group with said aqueous sample of step (b) on said solid support, under conditions wherein an antibody/antibody complex will form if said aqueous sample contains an antibody to *Mycoplasma*; (d) detecting the presence or absence of said first detectable group on said at least one solid support; (e) contacting an anti-IgM antibody coupled to a second detectable group, with said aqueous sample of step (b) on said solid support, under conditions wherein an antibody/antibody complex will form is said aqueous sample contains an antibody to *Mycoplasma*; and (f) detecting the presence or absence of said second detectable group on said at least one solid support, wherein detection of the presence of said first detectable group and/or of said second detectable group on said solid support detects *Mycoplasma* exposure in said subject.

In a further aspect, the present invention provides a method of detecting an antibody to *Mycoplasma* in a sample, comprising: (a) providing an aqueous sample; (b) contacting said aqueous sample to at least one solid support, each said at least one support having a mycoplasma antigen immobilized thereon, under conditions wherein an antigen/antibody complex will form if said aqueous sample contains an antibody to *Mycoplasma*; (c) contacting an anti-IgG antibody coupled to a first detectable group with said aqueous sample of step (b) on said solid support, under conditions wherein an antibody/antibody complex will form if said aqueous sample contains an antibody to *Mycoplasma*; (d) detecting the presence or absence of said first detectable group on said at least one solid support; (e) contacting an anti-IgM antibody coupled to a second detectable group, with said aqueous sample of step (b) on said solid support, under conditions wherein an antibody/antibody complex will form is said aqueous sample contains an antibody to *Mycoplasma*; and (f) detecting the presence or absence of said second detectable group on said at least one solid support, wherein detection of the presence of said first detectable group and/or of said second detectable group detects an antibody to *Mycoplasma* in said sample.

In the methods described herein, said at least one solid support can comprise two or more separate solid supports, and said contacting step (b) can comprise contacting a first portion of said sample to a first of said separate solid supports, and contacting a second portion of said sample to a second of said separate solid supports. As one nonlimiting example of such an embodiment, the composition and concentration of constituents in said first sample and in said second sample are the same.

In some embodiments of the methods described herein, said first detectable group and said second detectable group are the same and in some embodiments, said first detectable group and said second detectable group are different.

In some embodiments, said first detectable group and/or said second detectable group can comprise a detectable particle. In some embodiments, the particle can be a polymer particle, such as, e.g., a polystyrene particle, having a diameter of from about 50 nanometers to about 200 nanometers (e.g., about 50, 55, 60, 65, 70, 75, 80, 85, 90, 95, 100, 110, 120, 130, 140, 150, 160, 170, 180, 190, 200 nanometers).

In some embodiments, said first detectable group and/or said second detectable group can comprise a fluorescence moiety. Nonlimiting examples of a fluorescence moiety include a lanthanide chelate, such as a europium, terbium, samarium, and/or dysprosium chelate.

In some embodiments, said solid support can comprise an absorbent material, a nonlimiting example of which can be nitrocellulose.

In some embodiments, said anti-IgG antibody can comprise an anti-IgG heavy chain antibody. In some embodiments said anti-IgG antibody can be a monoclonal antibody, a polyclonal antibody, an antibody fragment or any other functional antibody now known or later identified.

In some embodiments, said anti-IgM antibody comprises an anti-IgM heavy chain antibody. In some embodiments, said anti-IgM antibody can be a monoclonal antibody.

In some embodiments, said mycoplasma antigen can comprise inactivated whole *Mycoplasma* (e.g., hydrogen peroxide inactivated whole *Mycoplasma*) and in some embodiments, said mycoplasma antigen can be *Mycoplasma bovis* (e.g., hydrogen peroxide inactivated whole *Mycoplasma bovis*).

In particular embodiments, said steps of the methods of this invention can be carried out in a lateral flow, dipstick, and/or flow through format.

In some embodiments, said aqueous sample can comprise, consist essentially of or consist of said biological fluid and an aqueous diluent. In particular embodiments, said aqueous diluent can comprise, consist essentially of or consist of raw whole milk that contains no detectable anti-*Mycoplasma* antibodies. In some embodiments, said raw whole milk can be collected from a subject (e.g., a cow) known to be uninfected by, and/or unexposed to, *Mycoplasma*.

In some embodiments, said biological fluid can comprise, consist essentially of or consist of milk and/or colostrum and in some embodiments, said aqueous sample can be filtered. In some embodiments, said milk and/or colostrums can be mixed with an aqueous diluent.

In some embodiments, said biological sample can comprise, consist essentially of or consist of blood or a blood fraction (e.g., blood plasma, serum, etc.).

In some embodiments, said detecting step (d) and/or said detecting step (f) can comprises quantitatively determining the amount of anti-*Mycoplasma* IgG antibodies and/or the amount of anti-*Mycoplasma* IgM antibodies in said biological fluid.

In some embodiments, said biological fluid can be collected from a mammalian subject. Nonlimiting examples of mammalian subjects of this invention include dairy cattle, beef cattle.

The methods of this invention can further comprise the steps of: (g) quantitatively determining the amount of anti-*Mycoplasma* IgG antibodies and the amount of anti-*Mycoplasma* IgM antibodies in said biological fluid; (h) calculating a value X by assigning a relative intensity value to the amount of anti-*Mycoplasma* IgG antibodies and a value Y by assigning a relative intensity value to the amount of anti-*Mycoplasma* IgM antibodies; (i) calculating a value Z by adding X and Y of step (h); and (j) identifying the subject as having Zone 1, Zone 2 of Zone 3 status regarding *Mycoplasma* exposure, wherein Zone 1 status is identified when Z is a high relative intensity value and indicates an active infection or recent exposure to mycoplasma, Zone 2 is identified when Z is a medium relative intensity value and indicates a prior exposure to mycoplasma, and Zone 3 is identified when Z is a low relative intensity value and indicates no prior exposure to mycoplasma.

When an image is acquired, the background and test line fluorescence intensity is captured through the optics and camera. The signal intensity is calculated by subtracting the background fluorescence from the test line fluorescence. This is done for both IgG and IgM, and then summed. The relative intensity is derived from the amount of antibody captured in a population (e.g., a cow herd population). Zone 3 represents culture confirmed non-infected subjects, while Zone 1 has generally culture confirmed positive subjects. Subjects that fall between these two zones are considered Zone 2.

In some embodiments, high, medium and low relative intensity values can be defined as:

High: equal to or greater than 75%; medium: from 74% to 26%; and low: equal to or less than 25%, including any number that falls within these ranges but not explicitly recited herein (e.g., equal to or greater than 75% can include 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 160, 170, 180, 190, 200, 300, 400, 500% or more; from 74% to 26% can include 74, 73, 72, 71, 70, 69, 68, 67, 66, 65, 64, 63, 62, 61, 61, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27 or 26%; and equal to or less than 25% can include 25, 24, 23, 22, 21, 20, 19, 18, 17, 16, 15, 14, 13, 12, 11, 10, 9, 8, 7, 6, 5, 4, 3, 2, 1 or 0%).

In other embodiments, high, medium and low relative intensity values can be defined as:

High: equal to or greater than 80%; medium: from 79% to 51%; and low: equal to or less than 50%, including any number that falls within these ranges but not explicitly recited herein.

In some embodiments, high, medium and low relative intensity values can be defined as:

High: equal to or greater than 90%; medium: from 89% to 16%; and low: equal to or less than 15%, including any number that falls within these ranges but not explicitly recited herein.

In particular embodiments of this invention, the methods of this invention can further comprise the steps of: (g) quantitatively determining the amount of anti-*Mycoplasma* IgG antibodies and the amount of anti-*Mycoplasma* IgM antibodies in said biological fluid using a QSCOUT™ signal reader instrument; (h) calculating a value X using the QSCOUT™ signal reader instrument; and (i) identifying the subject as having Zone 1, Zone 2 or Zone 3 status regarding *Mycoplasma* exposure, wherein Zone 1 status is identified when X is equal to or greater than 16 and indicates an active infection or recent exposure to mycoplasma, Zone 2 is identified when X is between 6 and 16 and indicates a prior exposure to mycoplasma, and Zone 3 is identified when X is equal to or less than 6 and indicates no prior exposure to mycoplasma.

In some embodiments, additional steps can be taken on the basis of identifying the subject as having Zone 1, Zone 2 or Zone 3 status as follows:

Zone 1: Antibody evidence in biological fluid of current or recent exposure to *Mycoplasma* spp. antigen. Recommended action: separate animal from herd and perform confirmatory polymerase chain reaction (PCR) testing.

*Mycoplasma* infection in dairy cattle is often resistant to antimicrobial therapy. Therefore, separation animals with suspected *Mycoplasma* infection is one of the best ways to minimize spreading the infection.

Zone 2: Antibody evidence in biological fluid of prior exposure to *Mycoplasma* spp. antigen. Recommended action: monitor animal with frequent testing (e.g., daily, weekly, monthly, bimonthly, quarterly, annually, etc.)

Zone 3: No evidence in biological fluid of prior exposure to *Mycoplasma* spp. antigen. No recommended action.

The present invention further comprises a composition, comprising, consisting essentially of and/or consisting of (a) an antigen, wherein said antigen an comprise, consist essentially of and/or consist of whole *Mycoplasma* inactivated with hydrogen peroxide; and (b) an absorbent support (e.g., nitrocellulose) to which said antigen is coupled or attached.

In some embodiments, the composition of this invention can further comprise (c) a housing (e.g., a lateral flow cassette housing) in which said absorbent support is contained.

In further embodiments, the composition of this invention can comprise, consist essentially of and/or consist of an antigen that is produced by the process of contacting said whole *Mycoplasma* with hydrogen peroxide for a time and at a concentration sufficient to kill said whole *Mycoplasma*, but insufficient to cause said whole *Mycoplasma* to lose the ability to specifically bind to both anti-*Mycoplasma* IgG antibodies and anti-*Mycoplasma* IgM antibodies.

In additional embodiments directed to the process for producing the antigen of this invention, the contacting step can be carried out by (i) combining said whole *Mycoplasma* and hydrogen peroxide in an aqueous solution for a time and at a concentration sufficient to kill said whole *Mycoplasma*, and then (ii) separating said whole *Mycoplasma* from said hydrogen peroxide before said whole *Mycoplasma* loses the ability to specifically bind to both anti-*Mycoplasma* IgG antibodies and anti-*Mycoplasma* IgM antibodies.

In some embodiments, the composition of this invention can comprise an absorbent support that is an elongate support. In some embodiments, the antigen of this invention can be coupled or attached to the absorbent support in the form of a strip or "stripe" (e.g., a strip or stripe perpendicular to the length dimension of the elongate support).

In some embodiments of the composition of this invention, the whole *Mycoplasma* can be *Mycoplasma Bovis*.

"Subjects" from which a biological fluid may be collected in carrying out the present invention are, in general, mammalian subjects, including human subjects and animal subjects for veterinary purposes. Animal subjects may include beef and milk cattle, pigs or swine, goats, sheep, rabbits, etc. Subjects may be of any age, including infant, neonate, adolescent, adult, and geriatric.

"Biological fluids" that may be collected from the subject for carrying out the present invention include, but are not limited to, blood or a fraction thereof (e.g., blood plasma), milk, colostrum, sputum, urine, cerebrospinal fluid, etc.

A sample of this invention can include a biological sample, such as a biological fluid and/or a solid and/or a semisolid sample obtained from a subject of this invention and can also include a liquid and/or a solid and/or a semisolid sample obtained from a source that is not a subject (e.g., a water sample, a food sample, a soil sample, a feed sample, a swab and/or washings from tools, instruments and/or other equipment used to maintain livestock, etc.)

"*Mycoplasma*" as used herein includes, but is not limited to, *M. californicum, M. pneumoniae, M. genitalium, M. bovis, M. bovigenitalium, M. alkalescens, M. arginini, M. gateae, M. canadense M. bovirhinis,* and any other *Mycoplasma* species now known or identified.

1. Antibodies and Detectable Groups.

Antibodies used in the present invention may be obtained from commercial sources, or produced in monoclonal or polyclonal form in accordance with known techniques.

In some embodiments, the anti-IgG antibody comprises an anti-IgG heavy chain antibody (e.g., a monoclonal antibody). A suitable example includes, but is not limited to, the BIG715A mouse anti-bovine IgG antibody, which is commercially available from VMRD Inc., P.O. Box 502, 425 NW Albion Drive, Pullman, Wash. 99163 USA, and from Gentaur LTD., Howard Frank Turnberry House, 1404-1410 High Road, Whetsone London N20 9BH, UK.

In some embodiments, the anti-IgM antibody comprises an anti-IgM heavy chain antibody (e.g., a monoclonal antibody). A suitable example includes, but is not limited to, the IL-A30 mouse anti-bovine IgM antibody, which is commercially available from Sigma Aldrich Corp., St. Louis, Mo., USA, and from BIO RAD, 4000 Alfred Nobel Drive, Hercules, Calif. 94547 USA).

The antibodies described above are generally labeled with or coupled to a detectable group, in accordance with known techniques. Any suitable detectable group may be used, include, but not limited to, fluorescent, luminescent, radioactive, and enzymatic detectable groups. Depending on the assay format, the detectable groups used for the two antibodies may be the same or different.

In some embodiments, the first and second detectable groups comprise a particle (e.g., a polymer particle, such as a polystyrene particle, having a diameter of from about 50 to about 200 nanometers, and in some embodiments, a diameter of about 100 nanometers).

In some embodiments, the first and second detectable groups comprise a fluorescent group (e.g., a lanthanide chelate, such as a europium, terbium, samarium, or dysprosium chelate).

In some particularly preferred embodiments, the first and second detectable groups comprise polymer particles as described above that further comprise a europium chelate.

2. Antigen.

The antigen is preferably an inactive, or killed, antigen, so that the products and methods of the invention do not themselves provide risk of infection. Yet, the antigen must be inactivated or killed in a way that they retain the effectiveness in the methods described herein.

In some embodiments, the antigen is produced by contacting whole *Mycoplasma* bacteria to hydrogen peroxide for a time and at a concentration sufficient to kill the *Mycoplasma*, but insufficient to cause the antigen to lose the ability to specifically bind to both anti-*Mycoplasma* IgG antibodies and anti-*Mycoplasma* IgM antibodies.

In some embodiments of the foregoing, the contacting step is carried by: (i) combining the *Mycoplasma* and hydrogen peroxide in an aqueous solution for a time and at a concentration sufficient to kill the *Mycoplasma*, and then (ii) separating (e.g., by dialysis, lyophilization, addition of catalase, or combination thereof) the *Mycoplasma* from the hydrogen peroxide before the antigen loses the ability to specifically bind to both anti-*Mycoplasma* IgG antibodies and anti-*Mycoplasma* IgM antibodies. The addition of catalase is considered as separating herein because the catalase consumes the available hydrogen peroxide and thereby quenches the reaction.

Once prepared, the antigen is coupled to a solid support, such as a nitrocellulose support, in accordance with known techniques. For a lateral flow assay the support will generally be an elongate support, and may include other segments such as a wicking pad, sample pad, and/or conjugate pad, again in accordance with known techniques, depending on the particular assay format. The antigen may typically be coupled to or deposited on the support in the form of a stripe (e.g., a stripe perpendicular to the length dimension of the elongate support). The support is typically packaged in a suitable cassette or cartridge, which may in turn include sample and reagent introduction wells and read-out windows, again depending upon the particular reading instrument employed.

Alternatively the test line antigen may be a recombinant and may be a single purified molecule and not a plurality of native antigens laid down on nitrocellulose as described above for the hydrogen peroxide inactivated whole organism. The recombinant may be produced in *E. coli*, Chinese hamster ovary (CHO) cells or yeast. The recombinant may be expressed alone or as a fusion protein. The recombinant antigen may consist of PG45, Vsp, Hsp60, P48 or the *Mycoplasma* immunogenic lipase (Mil A) 226 kDa Protein.

3. Assay Format and Procedures.

As noted above, the present invention may be implemented in a variety of assay formats, including but not limited to dipstick, flow-through, and lateral flow assay formats. Numerous variations of each thereof are known, and examples include but are not limited to those described in U.S. Pat. Nos. 5,798,273; 6,617,116; 7,270,995; 7,879,597; and 8,877,450.

A schematic overview of an assay of the invention is given in FIG. 1, where the dashed line represents the optional separation of the sequence of steps, and the optional separation of the solid support into two separate supports.

In general, and as noted above, the method includes the steps of:

(a) providing an aqueous sample comprising a biological fluid;

(b) contacting the sample to at least one solid support, each of at least one support having a *Mycoplasma* antigen immobilized thereon;

(c) contacting an anti-IgG antibody to at least one support, where the anti-IgG antibody is coupled to a first detectable group;

(d) detecting the first detectable group on at least one support;

(e) contacting an anti-IgM antibody to at least one support, where the anti-IgM antibody is coupled to a second detectable group; and (f) detecting the second detectable group on at least one support.

In some embodiments, at least one support comprises two separate supports, and the contacting step comprises: contacting a first portion of the sample to a first of the supports, and contacting a second portion of the sample to a second of the supports (e.g., where the composition and concentration of constituents in the first and second samples is the same). The two separate supports may be in the same cartridge or cassette, or in a separate cartridge or cassette. When separate, the cartridges or cassettes may be inserted into a reader sequentially or simultaneously, depending upon the physical configuration of the reader.

In general, the aqueous sample comprises the biological fluid in combination with an aqueous diluent. When the biological fluid comprises milk, the sample is preferably filtered, preferably after the milk or colostrums is mixed with the diluents (as discussed below). When the biological fluid comprises blood, a blood fraction, particularly blood plasma, is preferably employed.

Whether the biological sample comprises blood or blood fraction on the one hand, or milk or colostrums on the other, the diluent preferably itself contains milk: specifically, raw whole milk that is free of anti-*Mycoplasma* antibodies (e.g., collected from a cow known to be uninfected with *Mycoplasma*).

In some embodiments, the detecting step (d) and the detecting step (e) comprise quantitatively determining the amount of anti-*Mycoplasma* IgG and/or anti-*Mycoplasma* IgM antibodies in the biological sample. From this, the method may further comprise the step of: (f)generating, from the amount of anti-*Mycoplasma* IgG antibodies and/or anti-*Mycoplasma* IgM antibodies in the sample, a determination of *Mycoplasma* infection by the subject. Quantitative determination may be carried out with commercial reader instruments, such as discussed below, optionally modified in accordance with techniques known in the art.

In a particularly preferred embodiment, discussed further below, the determination of *Mycoplasma* infection may include a categorization of the sample as one showing: (i) no evidence of current or past infection or exposure to antigen of the subject; or (ii) evidence of past infection or exposure to antigen of the subject; or (iii) evidence of recent or current infection or exposure to antigen of the subject). The categorization may be carried out manually or, more preferably, by a software program running in a general-purpose computer, or with cloud-based software, or any suitable technique.

4. Imaging Reader

Figure 9:
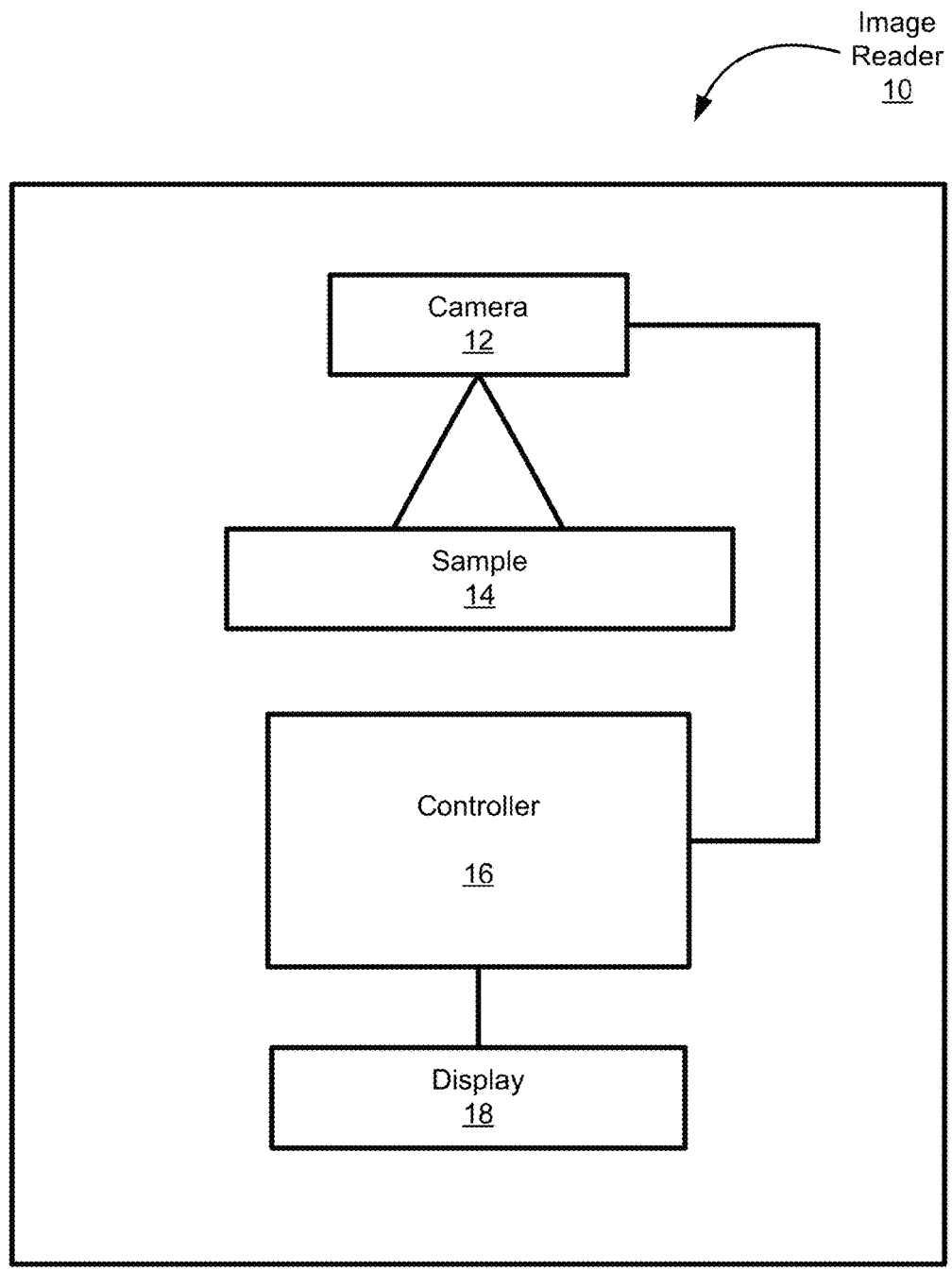
FIG. 9. A schematic diagram of an imaging reader for imaging a sample and calculating Zone 1, 2 and 3 determinations according to some embodiments.

An exemplary imaging reader 10 according to some embodiments is illustrated in FIG. 9. The imaging reader 10 includes a camera 12, a sample 14, a controller 16, and a display 18. As illustrated, the camera 12 is configured to image the sample 14, which may be inserted into the imaging reader 10, for example, using a sample cartridge. The camera 12 may include any optical components for imaging the sample, including a light source, lenses, and the like. The camera 12 may be any suitable imaging device, such as a CCD device, and may detect and produce digital images and/or intensity values of various signals, including signals indicating a quantitative amount of anti-*Mycoplasma* IgG and/or anti-*Mycoplasma* IgM. The imaging reader may be an automated microscope apparatus.

Individual components of the imaging reader 10 described herein may be as known in the art, or variations thereof that will be apparent to those skilled in the art based on the instant disclosure and prior automated microscopy apparatus such as described in U.S. Pat. No. 4,998,284 to Bacus; U.S. Pat. No. 5,790,710 to Price; U.S. Pat. No. 6,381,058 to Ramm; U.S. Pat. No. 6,929,953 to Wardlaw; U.S. Pat. No. 6,927,903 to Stuckey; U.S. Pat. No. 8,000,511 to Perz; U.S. Pat. No. 8,045,165 to Wardlaw; U.S. Pat. No. 8,081,303 to Levine; U.S. Patent Application Nos. 2001/0041347 to Sammak; or 2009/0233329 to Rodriguez. The imaging reader 10 may be a QSCOUT™ reader commercially available from Advanced Animal Diagnostics (Research Triangle Park, N.C., USA).

The controller 16 may include a computer processor and may be configured to receive intensity values and/or images from the camera 12 and to analyze the intensity values and/or images and to display the results on the display 18. For example, the controller 16 may be configured to:

(a) receive the anti-*Mycoplasma* IgG antibody intensity signal and the anti-*Mycoplasma* IgM antibody intensity signal from the image reader;

(b) calculate a value X by assigning a relative intensity value to the anti-*Mycoplasma* IgG antibody intensity signal and a value Y by and an anti-*Mycoplasma* IgM antibody intensity signal;
(c) calculate a value Z by adding X and Y of step (b); and
(d) identify the subject as having a Zone 1, Zone 2 or Zone 3 status regarding *Mycoplasma* exposure, wherein
Zone 1 status is identified when Z is a high relative intensity value and indicates an active infection or recent exposure to mycoplasma;
Zone 2 status is identified when Z is a medium relative intensity value and indicates a prior exposure to mycoplasma;
Zone 3 is identified when Z is a low relative intensity value and indicates no prior exposure to mycoplasma.

The controller 16 may be further configured to carry out various automated steps of the methods described herein.

A nonlimiting example of an apparatus of this invention is the QSCOUT® reader, which uses a 365 nm excitation light to induce fluorescence of European microspheres. The signal is passed through a focal lens and then through a 610 nm emission filter and then to a monochrome camera. Images are processed for signal intensity from the camera to the onboard PC (computer). Results are then displayed on the color touchscreen.

The present invention is explained in greater detail in the following non-limiting Examples.

EXAMPLES

Example 1

Determination of IgG and IgM Antibody Concentrations by ELISA

Figure 2:
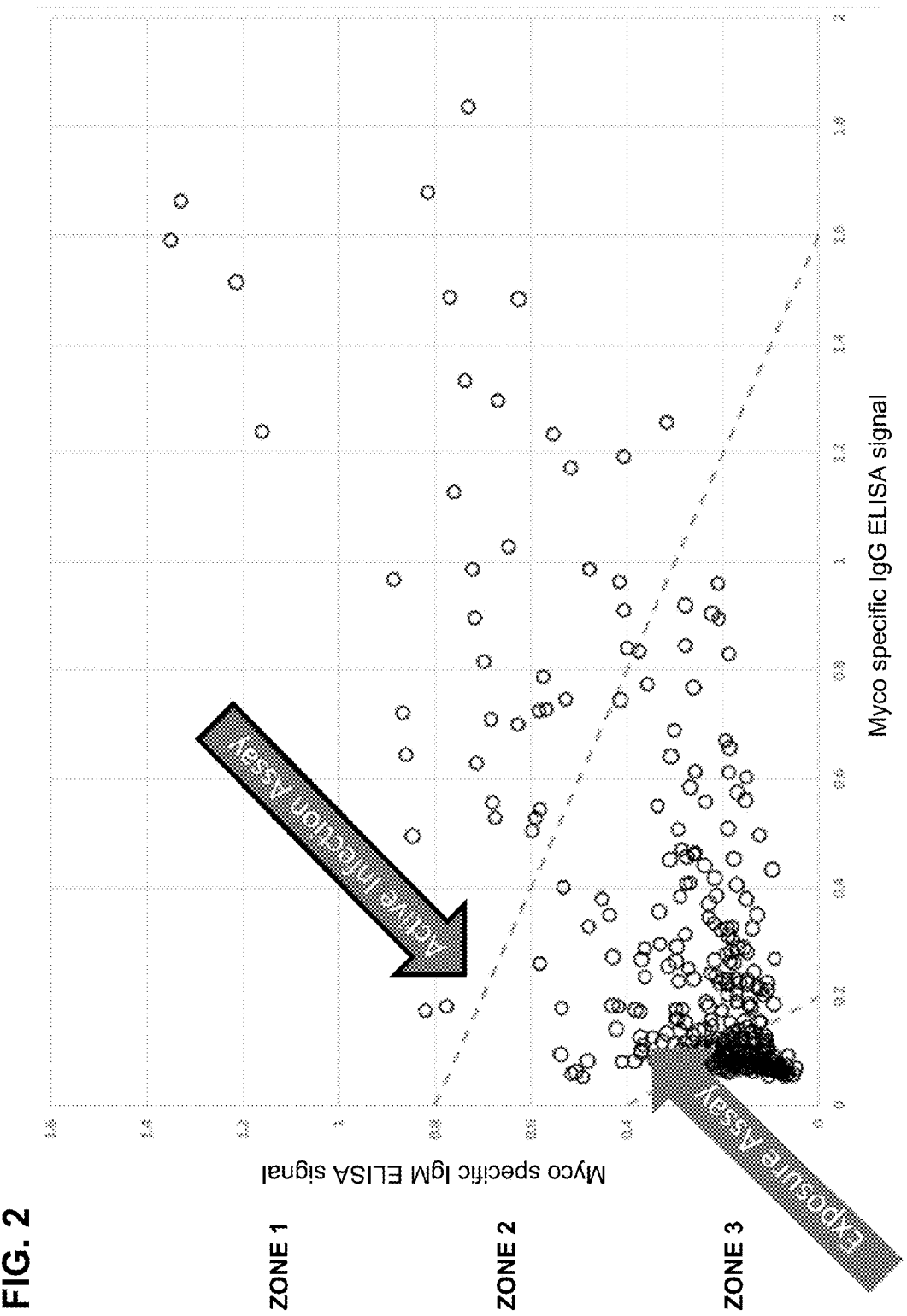
FIG. 2. Describes the relationship of specific mycoplasma IgG and IgM ab concentrations as determined by enzyme-linked immunosorbent assay (ELISA). Milk samples can fall into three zones based on the concentration of IgG antibodies (horizontal axis) and the concentration of IgM antibodies (vertical axis) in the sample.

The relationship of specific mycoplasma IgG and IgM antibody concentrations, as determined by enzyme-linked immunosorbent assay (ELISA), is graphically demonstrated in FIG. 2. Milk samples can fall into three zones based on the concentration of IgG antibodies (horizontal axis) and the concentration of IgM antibodies (vertical axis) in the sample. While numerous substantially equivalent phrasings may be used to describe the different zones, these zones may generally be described as:

Zone 3: No evidence of current or past infection or exposure to antigen of the subject;
Zone 2: Evidence of past infection or exposure to antigen of the subject;
Zone 1: Evidence of recent or current infection or exposure to antigen of the subject; Unfortunately, ELISA procedures are not suitable for "on-farm" use. Hence, we sought to develop a more simplified procedure, the preferred results of which are described below.

Example 2

Conjugate Preparation Procedure (Polystyrene-Europium Microsphere Coated With Antibody)

Ethyl dimethyl aminopropyl carbodiimide-HC1 (EDC or EDAC) coupling chemistry is used. Generally, the manufacturer's instructions, ThermoScientific, are followed. A one-stage coupling is used to conjugate the ThermoScientific Europium chelate carboxylated polystyrene microspheres with antibody before incorporation into lateral flow.

Particles of approximately 100 nm in size were selected for conjugation since these particles are expected to move easily through lateral flow assay membranes. Since these small microspheres are light in weight, higher centrifugation speeds and longer centrifugation times are usually required to process the conjugates.

Those skilled in the art will understand that a series of optimization experiments should be carried out with varying ratios and concentrations of microspheres to ligand and linking chemicals.

Example 3

Conjugation of Anti-Bovine IgM to ThermoScientific Eu Polystyrene Beads

Materials:
Anti-bovine IgG Mab IL-A30, Protein A-purified, 041816, LB, 3.75 mg/ml, PBS/0.05% NaN3.
Europium Chelate Microspheres-carboxylated: ex=365 nm, em=610 nm, 0.097 u, 1% solids
  Thermo Scientific Fluoro-Max, 93470350010150, mfg. lot 603780, 10 mg/ml DI water and 0.05% NaN3
HPLC water, Water, Ultra Pure, HPLC Grade, Aqua Solutions, Inc. W1089-10L
25 mM MES, pH 6 =Activation Buffer, Sigma 69890-10G, lot 1118827V, and Sigma 69890-50G
Zeba Spin Desalting Column, Thermo 87768, 2-ml, 40 kD MWCO, lot QI221343
Hula Mixer, sample mixer, Invitrogen version V.3PW
EDC (ethyl dimethyl aminopropyl carbodiimide-HC1), Sigma E6383, lot SLBL5188V
Microcentrifuge, Eppendorf 5424
Spectrophotometer, Eppendorf BioPhotometer Plus
Heat Systems Ultrasonics W-380 sonicator with C3 probe, 475 W max
Nutator rocker, Clay Adams brand
10% Tween 20, AMRESCO code M147-1L
PBS from 10× PBS, AMRESCO J373-4
BSA, 10% in PBS/ProClin 200 at 6 ppm, HPLC water JI IgG-free, 001-000-162
ProClin 200, Sigma 48171-U
Blocker: 0.5% BSA in PBST (HPLC water)+6 ppm ProClin
Wide-bore pipet tips, 250 ul, Rainin 17007102, Tips LTS W-0, RT-L-250
2.0-ml BioStar vials, screw cap, BioExcell cat. No. 49011151
1.7-ml microfuge tubes, PP, BioExpress Multi Max C-3269-1, lot 421457-X23045

Procedure:
Prepare 4 tubes where each tube has 200 ug protein/mg beads using 1.4 mg beads per prep.
Anti-bovine IgM Preparation:
1. Zeba column procedure, according to manufacturer Thermofisher's instructions, buffer exchange 1×525 ul antibody from PBS into 25 mM MES.
2. Allow EDC from freezer warm to room temp.
3. Determine protein conc. on spec. Blank vs. 25 mM MES. It is recommended that beads be at 1 mg/ml for coupling reaction:
4× Reaction

| Addn. order | 200 ug IgG/mg Thermo beads |
| --- | --- |
| 100 mM MES | 0.350 ml |
| HPLC water | 0.769 ml |

| Addn. order | 200 ug IgG/mg Thermo beads |
|---|---|
| Eu beads | 0.140 ml |
| α-IgM | 0.127 ml |
| EDC | 0.014 ml |

Total = 1.400 ml

Conjugation Procedure:
1. Pipet MES and water into a BioStar vial.
2. After vortexing well to resuspend beads, pipet, using wide-bore tip, beads into tube.
3. Vortex IgG and pipet appropriate volume into tube.
4. Mix tubes on Hula Mixer at 10 RPM, 1 min, 45°, 10, vibrate: 1°, 5 sec, being sure liquid moves from end to end.
5. Just before adding to beads, add MES to EDC to make a 10 mg/ml solution, vortex well to dissolve, and add 14 ul to the beads.
6. Mix tubes on Hula Mixer at above settings for 1-1.5 hr, covered.

Washing:
1. Transfer conjugate to microfuge tube using wide-bore tip.
2. Centrifuge at 10000×g for 30 min and remove supernatant. Resuspend pellet in 1 ml 25 mM MES with 10-sec sonication at Level 3 while sample on crushed ice.
3. Centrifuge 10000×g for 30 min., remove supernatant and resuspend in 25 mM MES Buffer and mix by sonication.
4. Repeat centrifugation at 10000×g (2' washing in MES buffer). Add 1000 ul PBST/PC +0.5% BSA. Sonicate while conjugate on ice to resuspend solids.
5. Mark 1.4 ml mark on tubes.
6. Then add more PBST/ProClin 200+0.5% BSA up to 1.4 ml mark. Label appropriately.
7. Cover with foil and placed on Nutator rocker to mix and block in refrigerator overnight.
8. Read A490 on final conjugate and calculate ug beads/ml by dividing A490 by 0.0012 as determined from unconjugated carboxylated Eu beads Example 4

Preparation of *Mycoplasma bovis* Antigen for Test Line (Culture/Purification/Inactivation)

The following procedure effectively renders the mycoplasma organism nonviable while preserving key immunoreactive epitopes. The inactivation of mycoplasma is accomplished with hydrogen peroxide (Fisher Product #S25360) followed by treatment with catalase (Sigma Cat C1345-1G), dialysis or lyophilization to stop the oxidation reaction. In this invention the $H_2O_2$ inactivated mycoplasma antigen is placed down on nitrocellulose and has been found to be stable enough for the execution of immunochromatographic assays "On Farm." While several strategies can be taken to stop the oxidation process and prevent over oxidation, catalase treatment is preferred. The concentration of inactivated whole organism placed down on the nitrocellulose is important, and those skilled in the art of preparing immunochromatographic assays will know the striping speed and concentration of stock antigen to be used. In a preferred embodiment of this process an Imagene contact striping instrument was used (Imagene Technology, PO Box 667, Hanover, N.H. 03755 USA), with an inactivated mycoplasma antigen stock as described herein in a concentration at 900 ug/ml.

Materials and Equipment. *Mycoplasma* isolate(s) found to be prevalent in the area being targeted with the commercial kit/Disposable inoculation loops, Greiner Bio-One 731171/*Mycoplasma* agar selective plated media, Udder Health Systems, Inc./Blood agar plates, Remel R01200/*Mycoplasma* Selective Broth, Udder Health Systems, Inc./CELLSTAR T-25 flask, Greiner Bio-One, 690190/CELLSTAR T-75 flasks, Greiner Bio-One, 658195/Electronic pipet, GeneMate P2006-1/Sterile serological pipettes, GeneMate P-2837-10 and P-2837-25/Sterile filter pipette tips, Rainin RT-L200FLR, RT-L1000FLR/Ethanol (reagent grade), Amresco E402-4L/Sterile 50-mL tubes, GeneMate C-3269-1/Sterile 1× PBS (ultra pure grade), Amresco K812-500ML/Biological hood/Immulon 4 HBX extra-high binding polystyrene microtiter plates, Thermo 62402-959/Pierce BCA Protein Assay Kit/Bovine Serum Albumin Standard (2 mg/mL vial)/BioTek plate reader/Multichannel pipet (p200)/Microcentrifuge tube/Hydrogen peroxide (35% stock), Fisher S25360/Catalase, Sigma C1345/1× PBS, Amresco J373-4L

*Mycoplasma bovis* Propagation, Purification and Determination of Concentration by Total Protein.

Steps:

1. Inoculate a T-25 flask containing 12 mL of *Mycoplasma* broth with 200 μL of *M. bovis* frozen stock. Incubate at 37° C. in 10% $CO_2$.
2. When turbid, use a 10-mL serological pipette to wash the surface of the T-25 flask 3× with its own contents. Use the T-25 flask to inoculate 3 T-75 flasks containing 70 mL of *Mycoplasma* broth with 4 mL of bug at log phase. Incubate at 37° C. in 10% $CO_2$.
3. After becoming turbid, use a 25-mL serological pipette to wash the surface of the T-75 flasks 3× with their own contents and transfer the contents from the T-75 flask into four sterile 50-mL tubes. Use a 25-mL serological pipette to aliquot sterile 1× PBS into separate sterile 50-mL tube(s) for each *Mycoplasma* species that will be purified.
4. Centrifuge for 25 minutes at 4000 RPM then decant the old media into waste tubes.
5. Combine contents into 2 common tubes: Use a 10-mL serological pipette to add 4 mL of 1× PBS to two of the tubes. Aspirate to resuspend the pellets and transfer the contents into the other two tubes. Use a p1000 pipette with sterile tips to add 1 mL of sterile PBS into the initial two tubes. Rinse the tubes with the PBS and transfer to the tubes that now contain the resuspended organism. Aspirate to mix.
6. Centrifuge for 25 minutes at 4000 RPM then decant the old media into waste tubes. Resuspend the organism with 5 mL of PBS in each tube.
7. Repeat step 6 twice more.
8. Centrifuge for 20 minutes at 4000 RPM then decant the old media into waste tubes.
9. Combine the contents into 1 tube: Use a 5-mL serological pipette to add 2 mL of 1× PBS to one of the tubes. Aspirate to resuspend the pellets and transfer the contents into the other tube. Use a p1000 pipette with sterile tips to add 2 mL of sterile PBS into the initial tube. Rinse the tubes with the PBS and transfer to the tube that now contains the resuspended bugs. Aspirate to mix.
10. Perform a protein assay such as Pierce Bicinchoninic Assay (BCA) on the concentrated and washed organism stock. Multiply BCA concentration (µg/mL) by total volume (mL). The total yield should be approximately 10 mg of bug. Calculate total yield.

Inactivation of the Purified *Mycoplasma bovis* Whole Organism with Hydrogen Peroxide and Quenching the Oxidation Reaction. The antigen is typically killed prior to striping on nitrocellulose membrane supported by card. Hydrogen peroxide ($H_2O_2$) is used at 1% (v/v) for 30 min at room temp. The reaction is stopped by the addition of catalase, which is added to a final working concentration of 20 µg/mL and incubated for 15 min at 37° C. (the optimal temperature for catalase activity). The final protein mycoplasma antigen concentration is 900 µg/mL. The concentration of the antigen changes from batch to batch, so the total protein recovered after processing will vary with lot. The concentration of hydrogen peroxide to add is determined by BCA assay calculations. The organism concentration is typically diluted to 900 ug/ml concentration then the hydrogen peroxide is added.

Steps:
1. Calculate the volumes of organisms, $H_2O_2$, catalase, and PBS needed (150 µL total volume, with the goal of achieving a final stock that is 900 µg/mL of organism, 1% v/v-$H_2O_2$ and 20-ug/ml Catalase.
2. Dilute organism in 1× PBS in a microcentrifuge tube to achieve the target 900 ug/ml protein concentration.
3. Add $H_2O_2$ to a final concentration of 1% v/v and let the sample sit for 30 min at room temp.
4. Add catalase to a final 20 µg/mL concentration and let the sample incubate for 15 min at 37° C.

Agitate the sample by hand shaking to make the bubbles rise to the surface of the tube. The final oxidized sample is ready for striping down on nitrocellulose after the 30 minute hydrogen peroxide treatment and 15 minute catalase treatment, or can be stored at 4°.

Alternatively the purified *Mycoplasma* organism can be killed with 1% v/v hydrogen peroxide when the antigen sample concentration ranges from 600 ug/ml to 1200 ug/ml. Alternatively the purified *Mycoplasma* organism is at a concentration of 900 ug/ml and a concentration of 0.5% v/v hydrogen peroxide to 3% v/v hydrogen peroxide is added to achieve complete inactivation of the mycoplasma organism.

Example 5

Milk Sample Specimen Processing for *Mycoplasma* Antibody Lateral Flow Assay

Milk samples are diluted to a final ratio of 1:5 or 1 part to 4 parts. The processing can be performed on freshly collected milk samples which are still body temperature, milk samples that have been retrieved from a refrigerator and/or milk samples that have been frozen and thawed for testing.

The final specimen dilution is 1:1:3 (Specimen for testing: Negative mycoplasma ab milk for normalization:Specimen Diluent "D" containing 1.3M NaCl, 50 mM Tris, 0.2% w/v BSA and 6 ppm ProClin) for a final dilution of 1:5. The solution is then immediately filtered with cat 02-681-52 or a device with an equivalent porosity. The sequence of first diluting and then filtering was found to be preferred. Only a minimal amount of processed sample (typically 50 ul) needs to be recovered from the permeate side of the Porex frit within the filter to perform the assay. Usually a total diluted milk volume of about 1 ml is sufficient to recover the necessary amount of processed milk for lateral flow assay. The diluted then filtered milk sample can be stored at 4° C. until ready for LFA testing or frozen (−20° C. to −80° C.) for longer periods.

Materials:
1. Raw milk sample
2. Standard serum filters, 16 mm diameter (Fisherbrand Cat #02-681-52)
3. Capital vial 13-mL flip-top vials with an inner diameter which matches the serum filter width (Thermo Cat # VETHC1500)
4. Specimen diluent, Solution D (Table 1), complete with normalization milk and supplemental blocker (Table 2)
5. Transfer pipets (disposable exact volume) for moving raw milk into the Cat 02-681-52 device and transferring the processed milk to the lateral flow specimen pad.

Method:
Typically 800 ul of the complete Specim,en Diluent "D" is placed in the flip-top vial or inside the Fisherbrand device. Two-hundred microliters of raw milk specimen is then removed from the bulk collection sample, either quarter or composite, and added to the diluent. The combined 1 ml volume can be mixed within these disposables and the Fisherbrand Filter advanced or pulled to draw permeate through the separation device. In just 1-2 steps, usually requiring seconds, a processed milk sample is ready for application to the lateral flow cassette. The processed sample is ready for application to a specimen pad such as GE CF4 or Millipore C048.

Example 6

Blood Sample Specimen Processing for *Mycoplasma* Antibody Lateral Flow Assay

Obtaining blood plasma from whole blood can be achieved before applying the sample to the lateral flow device or whole blood can be applied to a lateral flow specimen pad equipped to retain cells and allow plasma to wick forward to the nitrocellulose reaction pad.

No matter where the separation occurs, within the cassette or offline, the first step in recovering blood plasma is to collect whole blood into anticoagulant-treated tubes. EDTA-treated (lavender tops), citrate-treated (light blue tops) or heparinized tubes (green tops) are nonlimiting examples of acceptable tubes.

If desirable to separate blood plasma from cells off line, blood can be centrifuged for 10 minutes at 1,000-2,000×g using a refrigerated centrifuge. Following centrifugation, the liquid component (plasma) is immediately transferred into a clean polypropylene tube using a Pasteur pipette. The samples should be maintained at 2-8° C. while handling. If the plasma is not analyzed immediately, the plasma can be portioned into smaller aliquots, stored, and transported at −20° C. or lower.

If a centrifuge is not available, cells can be separated from plasma in minutes by applying the whole blood sample to the MDI Product RPSD-450 Cat B450 (Advanced Microdevices PVT.LTD. 21 India, Area, Ambala CANTT. 133 006 India) or an equivalent device.

For processing blood plasma in advance of the mycoplasma antibody assay, the dilution of the plasma component is done after plasma is separated from cells. Blood plasma samples are diluted to a final 1:20 for testing. For example the 1:20 dilution may be accomplished by first diluting the plasma 1:4 in phosphate buffered saline (PBS) and then 1:5 with diluent. The processing can be performed on freshly collected samples which are still body temperature and/or samples that have been retrieved from a refrigerator after e.g., an overnight hold at 2-8° C. Once plasma has been recovered, the liquid portion of blood can be diluted 1:4:16 (specimen for testing:negative mycoplasma ab milk for normalization:specimen Diluent "D", containing 1.3M NaCl) for a final dilution of 1:20. Usually a total diluted plasma volume of 50 ul is all that is required to initiate the lateral flow assay. The filtered and then diluted blood plasma sample can be stored at 4° C. until ready for LFA testing or frozen (−20° C. to −80° C.) for longer periods.

Materials:
1. whole blood anticoagulated specimen
2. MDI Product RPSD-450 or centrifuge
3. Capital vial 13-mL flip-top vials with an inner diameter which matches the serum filter width of Thermo Cat # VETHC1500.
4. Specimen diluent, Solution D (Table 1), complete with normalization milk and supplemental blocker (Table 2)
5. Transfer pipers (disposable exact volume) for moving raw blood into the MDI Product RPSD-450.
6. Device for transferring the processed plasma into diluent and for removing diluted plasma and transferring to lateral flow specimen pad.

Detailed Method Involving Plasma Prepared by Centrifugation:

Typically 800 ul of the complete Specimen Diluent "D" is placed in the flip-top vial. Two-hundred microliters of blood plasma specimen is then added and mixed with diluent. The combined 1 ml volume can be mixed within these disposables in just 1-2 steps, usually requiring a few minutes. The processed sample is ready for application to a lateral flow cassette equipped with a specimen pad, such as GE CF4 or Millipore C048.

Example 7

Working Stock Solutions, Components and Concentrations

Three solutions are used in preparation of the lateral flow membrane card to include the specimen side-arm when required (A, B and C). Two additional solutions are used in the execution of the lateral flow assay. The blocking solution "C" is placed on the conjugate pad after solutions A and B are applied. The blocking solution "C" is also applied to the specimen pad before cassette assembly. Solution "A" is applied to the glass fiber conjugate pad before the europium detector is laid down. Solution "B" contains the Eu detector particle and is applied to the conjugate pad after Solution "A" is thoroughly dry. All milk and blood plasma specimens can be diluted with Solution "D." Solution "E" is the last reagent added to the LFA test strip when the assay is being conducted. Solution "E" hydrates the prepositioned detector and moves the europium based reagent across the nitrocellulose to the wicking pad.

Example 8

Example of Lateral-Flow Assay (LFA) Cartridges

FIGS. 3A-3B are exterior and interior schematic illustrations of a side-arm lateral flow assay cartridge (side arm angled 1-90 degrees from main backer card). The side-arm is typically removed after specimen addition, and not present during test line signal generation. The side-arm may be in contact with the nitrocellulose, the conjugate pad, or both.

FIGS. 4A-4B are exterior and interior schematic illustrations of a two-hole lateral flow assay cartridge (no side-arm required). The second hole provides access to the conjugate pad and/or nitrocellulose.

Example 9

Determination of IgG and IgM Antibody Concentrations by LFA

This example was carried out in accordance with the methods, reagents, products and procedures described in Examples 2-8 above.

Figure 5:
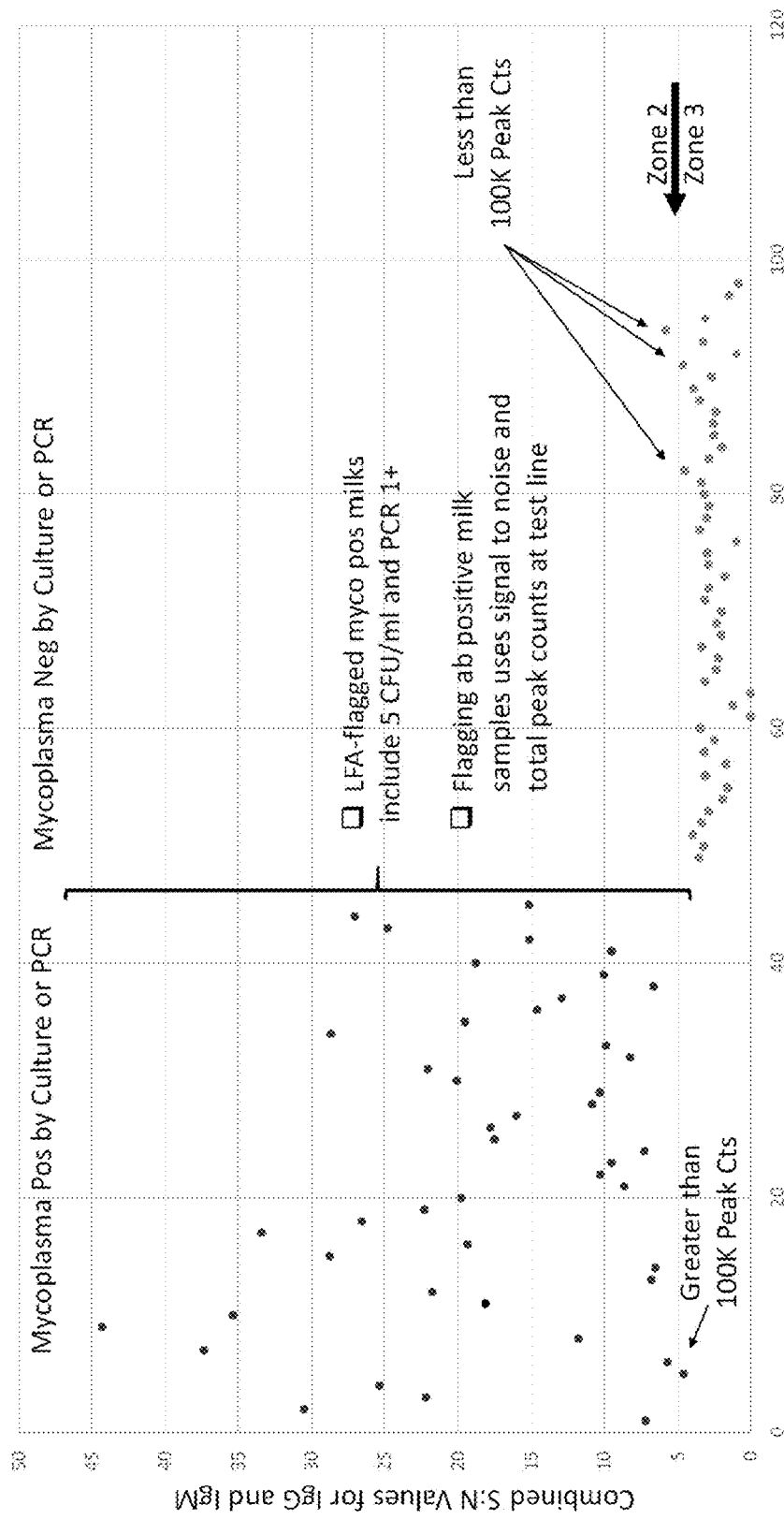
FIG. 5. Graphic demonstrating that a lateral flow assay format, suitable for "on farm" use, has the ability to discern antibody positive from antibody negative specimens (Zone 2 from Zone 3), as shown previously by ELISA.

FIG. 5 graphically demonstrates that a lateral flow assay format, suitable for "on farm" use, has the ability to discern antibody positive from antibody negative specimens (Zone 2 from Zone 3), as shown previously by ELISA.

Example 10

Determination of IgG and IgM Antibody Concentrations by LFA and a Commercial Strip Reader This example was carried out in accordance with the methods, reagents, products and procedures described in Examples 2-8 above.

Figure 6:
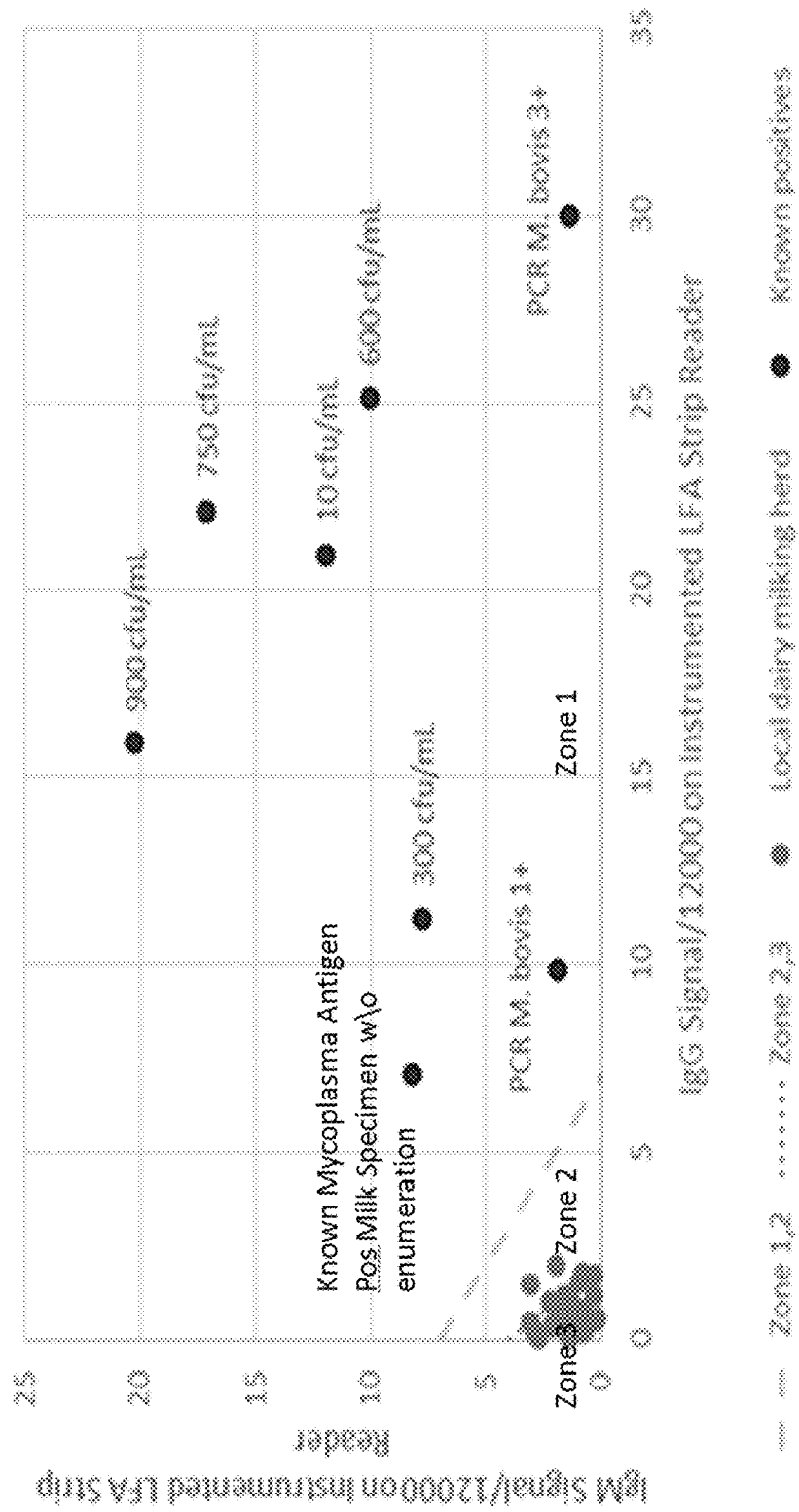
FIG. 6. Illustration of Zones 1, 2 and 3 reestablished with lateral flow assay and a commercial instrumented lateral flow strip reader.

FIG. 6 shows zones 1, 2 and 3 reestablished with a lateral flow assay cartridge and method, and a commercial instrumented lateral flow strip reader. Bacterial free milks and milks infected with other bacteria that cause mastitis, other than *Mycoplasma* do not enter Zone 1. Only milk containing heavy concentrations of mycoplasma specific antibody reach Zone 1. All of the Zone 1 milks were separately confirmed as having mycoplasma antigen present by either culture or PCR.

Exampel 11

Determination of IgG and IgM Antibody Concentrations by LFA and a QSCOUT™ Reader This example was carried out in accordance with the methods, reagents, products and procedures described in Examples 2-7 above.

Figure 7:
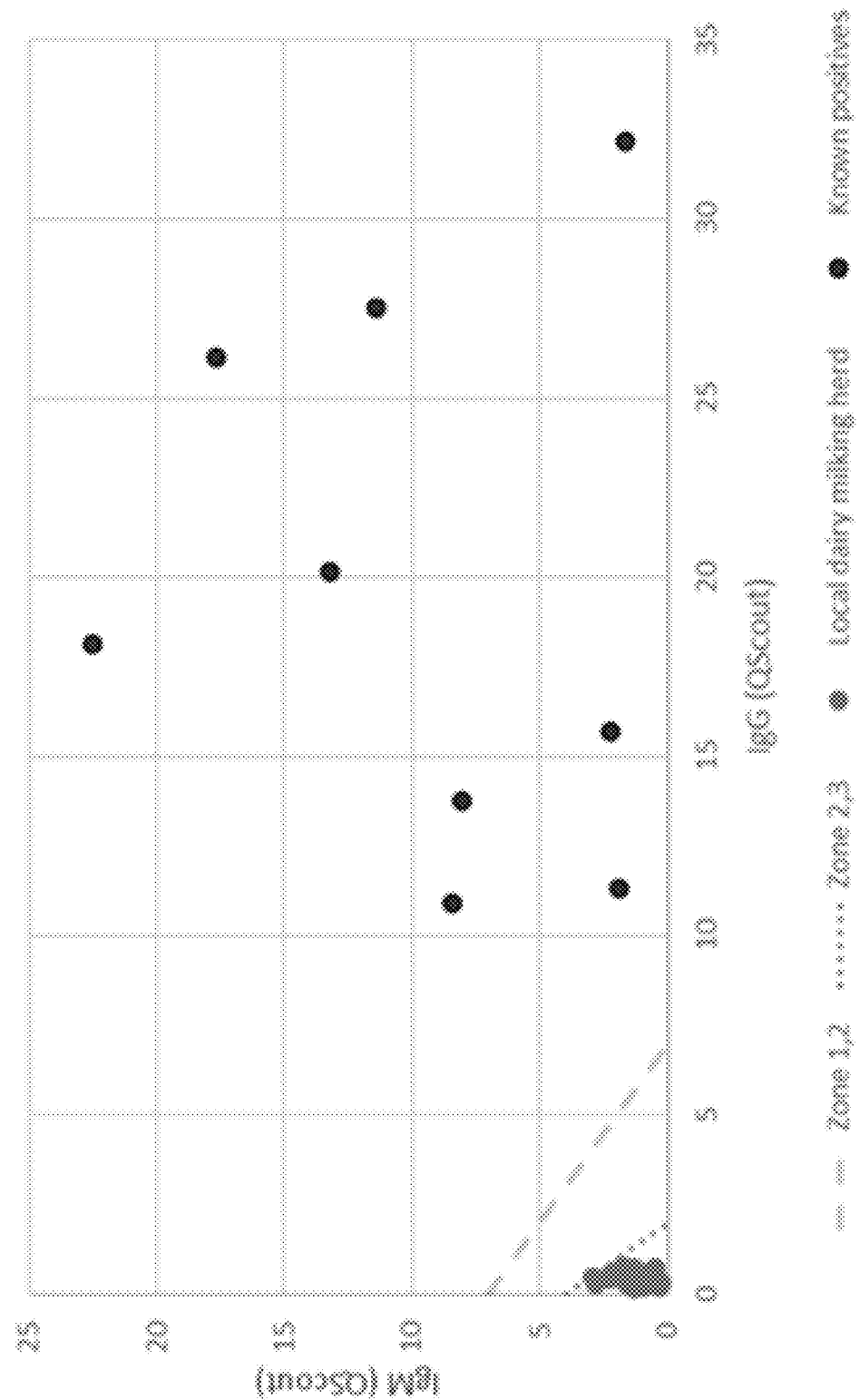
FIG. 7. Zone 1 to 3 reestablished with lateral flow assay and a QSCOUT™ reader.
Figure 8:
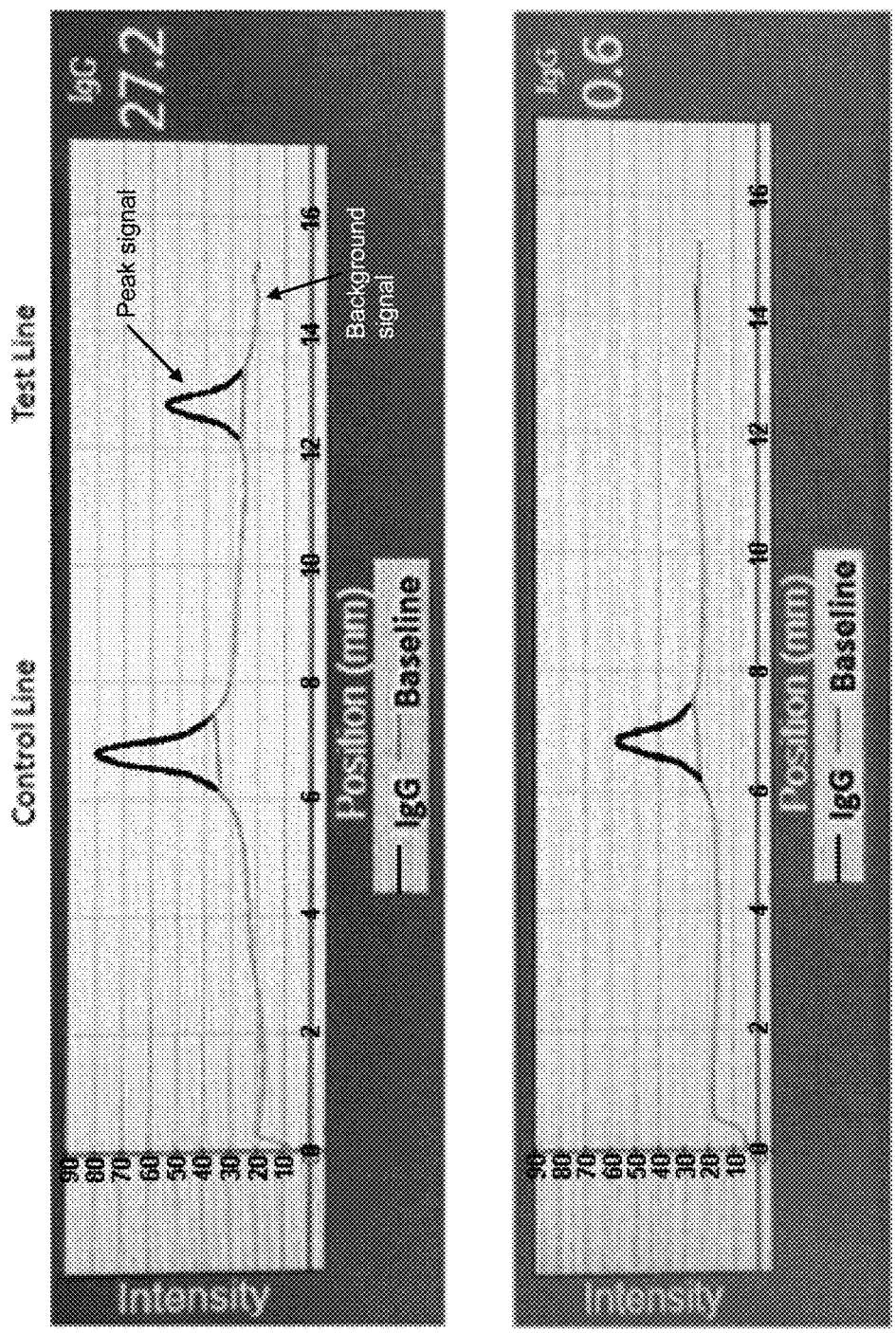
FIG. 8. Exemplary calculation of X based on signal output in a QSCOUT™ reader. X is calculated from FIG. 8 as follows: IgG signal is fluorescence at test line minus background on IgG test. IgM signal is fluorescence at test line minus background on IgM test. X is the sum of IgG signal and IgM signal. In some embodiments, X could also be weighted sum, or an average.

FIG. 7 shows Zones 1, 2, and 3 reestablished with a lateral flow assay cartridge and method, and a QSCOUT™ reader (available from Advanced Animal Diagnostics, Inc., 633 Davis Drive, Suite 460, Morrisville, N.C., 27560 USA). Bacterial free milks and milks infected with other bacteria that cause mastitis, other than mycoplasma do not enter Zone 1. Only milk containing heavy concentrations of mycoplasma specific antibody reach Zone 1. All of the Zone 1 milks were separately confirmed as having mycoplasma antigen present by either culture or PCR. The inventors have found that the milk samples in Zone 1 can have an agreement with positive culture and or positive PCR that is 85% or greater. In other words the inventors have made an unexpected finding that a certain type of IgG-IgM antibody signature, as found in Zone 1, has a strong correlation to the presence of *Mycoplasma* species antigen in the milk sample as measured by culture and or polymerase chain reaction. The correlation can be 85%, 86%, 87%, 88%, 89%, 90%, 91%, 92%, 93%, 94%, 95%, 96%, 97%, 98%, 99% or 100%.

Example 12

Blood Plasma Tested for *Mycoplasma* Antibody by LFA

This example was carried out in accordance with the methods, reagents, products and procedures described in Examples 2-7 above. As shown in Table 3 below, a good correlation of results was obtained with blood samples and milk samples from the same subject.

The foregoing is illustrative of the present invention, and is not to be construed as limiting thereof The invention is defined by the following claims, with equivalents of the claims to be included therein.

TABLE 1

| Soln A<br>Glass Fiber Pad<br>Prep | Soln B<br>Conjugate<br>Storage and Dry<br>Down Buffer | Soln C<br>Blocker | Soln D<br>Specimen<br>Diluent | Soln E<br>Chaser<br>Solution |
|---|---|---|---|---|
| PBS (Amresco Co.Formula Cat J373-4L) 10x used to prepare 1X. | PBS (Amresco Co. Formula Cat J373-4L) 1X | Tris 50 mM pH 8 | Tris 50 mM pH 8 | Tris 50 mM pH 8 |
| | ProClin 6 ppm<br>BSA 0.5% w/v | NaCl 200 mM<br>ProClin 6 ppm<br>BSA 0.2% w/v | NaCl 1.3M<br>ProClin 200 6 ppm<br>BSA 0.2% w/v | NaCl 780 mM<br>ProClin 6 ppm<br>BSA 0.2% w/v |
| H2O | H2O | H2O<br>Fish Gelatin 6% w/v | H2O | H2O |
| Sucrose 10% w/v | | | | |
| | Tween 0.15% v/v | | | |
| | | | Mix the above with Supplemental Blocker for a final 5% v/v<br>Mix the above Soln D containing supplemental with Myco Neg Milk Normalizer and specimen, 1:1:3 respectively. | Mix the above with Supplemental Blocker for a final 5% v/v |

Note:
BSA is always protease free and IgG free.

TABLE 2

Supplemental Blocker

| Ingredient | Final Concentration |
|---|---|
| Potassium Phosphate Monobasic | $6.25 \times 10^{-3}$ M |
| Potassium Phosphate Dibasic | $1.86 \times 10^{-2}$ M |
| Casein | 0.2% |
| Sodium Hydroxide | $8.36 \times 10^{-3}$ N |
| Boric Acid | 0.5% |
| Sucrose | 0.02% |
| Surfactant 10 G | 0.1% |
| Polyvinyl alcohol (PVA) | 0.5% |
| Sodium Azide | 0.05% |

TABLE 3

Correlation between milk and blood plasma results generated with lateral flow assay for *Mycoplasma* antibody.[1]

| Prior *Mycoplasma* PCR or Culture Results | Cow ID | Milk LFA IgG (S:N) | Plasma LFA IgG (S:N) |
|---|---|---|---|
| Pos for Agn | 15427 | 33.16 | 66.16 |
| Pos for Agn | 11240 | 23.80 | 49.34 |
| Pos for Agn | 92188 | 10.04 | 9.53 |
| Pos for Agn | 5228 | 3.35 | 6.69 |
| Known Neg for Agn | 4114 | 1.00 | 1.00 |

[1]S:N values above 3 are considered positive for mycoplasma-specific antibody. The S:N value is the Signal at the test line (above the baseline trace) for a positive antibody specimen is divided by the signal for a negative antibody specimen.

What is claimed is:

1. A method of detecting *Mycoplasma* exposure in a subject, comprising:
    (a) providing an aqueous sample comprising a biological fluid from the subject;
    (b) contacting said aqueous sample to at least one solid support, each said at least one support having a mycoplasma antigen immobilized thereon, under conditions wherein an antigen/antibody complex will form if said aqueous sample contains an antibody to *Mycoplasma*;
    (c) contacting an anti-IgG antibody coupled to a first detectable group with said aqueous sample of step (b) on said solid support, under conditions wherein an antibody/antibody complex will form if said aqueous sample contains an antibody to *Mycoplasma*;
    (d) detecting the presence or absence of said first detectable group on said at least one solid support;
    (e) contacting an anti-IgM antibody coupled to a second detectable group, with said aqueous sample of step (b) on said solid support, under conditions wherein an antibody/antibody complex will form if said aqueous sample contains an antibody to *Mycoplasma* ; and
    (f) detecting the presence or absence of said second detectable group on said at least one solid support, wherein detection of the presence of said first detectable group and/or of said second detectable group on said solid support detects *Mycoplasma* exposure in said subject, wherein said aqueous sample comprises said biological fluid and an aqueous diluent; and wherein said aqueous diluent comprises raw whole milk that contains no detectable anti-*Mycoplasma* antibodies.

2. The method of claim 1, wherein said at least one solid support comprises two separate supports, and said contacting step (b) comprises contacting a first portion of said sample to a first of said solid supports, and contacting a second portion of said sample to a second of said solid supports.

3. The method of claim 1, wherein said first detectable group and said second detectable group are the same.

4. The method of claim 1, wherein said first detectable group and/or said second detectable group comprises a detectable particle.

5. The method of claim 1, wherein said first detectable group and/or said second detectable group comprises a fluorescence moiety.

6. The method of claim 1, wherein said solid support comprises an absorbent material.

7. The method of claim 1, wherein said anti-IgG antibody comprises an anti-IgG heavy chain antibody.

8. The method of claim 1, wherein said anti-IgM antibody comprises an anti-IgM heavy chain antibody.

9. The method of claim 1, wherein said mycoplasma antigen comprises inactivated whole *Mycoplasma*.

10. The method of claim 1, wherein said mycoplasma antigen is from *Mycoplasma bovis*.

11. The method of claim 1, wherein said steps are carried out in a lateral flow, dipstick, or flow through format.

12. The method of claim 1, wherein said biological fluid comprises milk, and said aqueous sample is filtered.

13. The method of claim 1, wherein said biological sample comprises blood or a blood fraction.

14. The method of claim 1, wherein said detecting step (d) and/or said detecting step (f) comprises quantitatively determining the amount of anti-*Mycoplasma* IgG antibodies and/or the amount of anti-*Mycoplasma* IgM antibodies in said biological fluid.

15. The method of claim 1, wherein said biological fluid is collected from a mammalian subject.

16. A method of detecting *Mycoplasma* exposure in a subject, comprising:
(a) providing an aqueous sample comprising a biological fluid from the subject;
(b) contacting said aqueous sample to at least one solid support, each said at least one support having a mycoplasma antigen immobilized thereon, under conditions wherein an antigen/antibody complex will form if said aqueous sample contains an antibody to *Mycoplasma*;
(c) contacting an anti-IgG antibody coupled to a first detectable group with said aqueous sample of step (b) on said solid support, under conditions wherein an antibody/antibody complex will form if said aqueous sample contains an antibody to *Mycoplasma*;
(d) detecting the presence or absence of said first detectable group on said at least one solid support;
(e) contacting an anti-IgM antibody coupled to a second detectable group, with said aqueous sample of step (b) on said solid support, under conditions wherein an antibody/antibody complex will form if said aqueous sample contains an antibody to *Mycoplasma* ; and (f) detecting the presence or absence of said second detectable group on said at least one solid support, wherein detection of the presence of said first detectable group and/or of said second detectable group on said solid support detects *Mycoplasma* exposure in said subject, further comprising the steps of:
(g) quantitatively determining the amount of anti-*Mycoplasma* IgG antibodies and the amount of anti-*Mycoplasma* IgM antibodies in said biological fluid;
(h) calculating a value X by assigning a relative intensity value to the amount of anti-*Mycoplasma* IgG antibodies and a value Y by assigning a relative intensity value to the amount of anti-*Mycoplasma* IgM antibodies;
(i) calculating a value Z by adding X and Y of step (h); and
(j) identifying the subject as having Zone 1, Zone 2 of Zone 3 status regarding *Mycoplasma* exposure, wherein
Zone 1 status is identified when Z is a high relative intensity value and indicates an active infection or recent exposure to mycoplasma,
Zone 2 is identified when Z is a medium relative intensity value and indicates a prior exposure to mycoplasma, and
Zone 3 is identified when Z is a low relative intensity value and indicates no prior exposure to mycoplasma.

17. The method of claim 1, further comprising the steps of:
(g) quantitatively determining the amount of anti-*Mycoplasma* IgG antibodies and the amount of anti-*Mycoplasma* IgM antibodies in said biological fluid using an imaging reader instrument;
(h) calculating a value X using the imaging reader instrument; and
(i) identifying the subject as having Zone 1, Zone 2 or Zone 3 status regarding *Mycoplasma* exposure, wherein
Zone 1 status is identified when X is equal to or greater than 16 and indicates an active infection or recent exposure to mycoplasma,
Zone 2 is identified when X is between 6 and 16 and indicates a prior exposure to mycoplasma, and
Zone 3 is identified when X is equal to or less than 6 and indicates no prior exposure to mycoplasma.

18. An apparatus for determining *Mycoplasma* exposure in a subject, the apparatus comprising:
an imaging reader configured to image a sample having an anti-*Mycoplasma* IgG antibody intensity signal and an anti-*Mycoplasma* IgM antibody intensity signal; and
a controller configured to
(a) receive the anti-*Mycoplasma* IgG antibody intensity signal and the anti-*Mycoplasma* IgM antibody intensity signal from the image reader;
(b) calculate a value X by assigning a relative intensity value to the anti-*Mycoplasma* IgG antibody intensity signal and a value Y by assigning a relative intensity value to the anti-*Mycoplasma* IgM antibody intensity signal;
(c) calculate a value Z by adding X and Y of step (b); and
(d) identify the subject as having a Zone 1, Zone 2 or Zone 3 status regarding *Mycoplasma* exposure, wherein
Zone 1 status is identified when Z is a high relative intensity value and indicates an active infection or recent exposure to mycoplasma;
Zone 2 status is identified when Z is a medium relative intensity value and indicates a prior exposure to mycoplasma;

Zone 3 is identified when Z is a low relative intensity value and indicates no prior exposure to mycoplasma.

19. The apparatus of claim 18, wherein the high relative intensity value of Zone 1, the medium relative intensity value of Zone 2 and the low relative intensity value of Zone 3 are determined empirically from clinical symptoms.

20. The apparatus of claim 18, wherein the sample comprises a lateral flow assay.

21. The method of claim 16, wherein said at least one solid support comprises two separate supports, and said contacting step (b) comprises contacting a first portion of said sample to a first of said solid supports, and contacting a second portion of said sample to a second of said solid supports.

22. The method of claim 16, wherein said first detectable group and said second detectable group are the same.

23. The method of claim 16, wherein said first detectable group and/or said second detectable group comprises a detectable particle.

24. The method of claim 16, wherein said first detectable group and/or said second detectable group comprises a fluorescence moiety.

25. The method of claim 16, wherein said solid support comprises an absorbent material.

26. The method of claim 16, wherein said anti-IgG antibody comprises an anti-IgG heavy chain antibody.

27. The method of claim 16, wherein said anti-IgM antibody comprises an anti-IgM heavy chain antibody.

28. The method of claim 16, wherein said mycoplasma antigen comprises inactivated whole *Mycoplasma*.

29. The method of claim 16, wherein said mycoplasma antigen is from *Mycoplasma bovis*.

30. The method of claim 16, wherein said steps are carried out in a lateral flow, dipstick, or flow through format.

31. The method of claim 16, wherein said biological fluid comprises milk, and said aqueous sample is filtered.

32. The method of claim 16, wherein said biological sample comprises blood or a blood fraction.

33. The method of claim 16, wherein said detecting step (d) and/or said detecting step (f) comprises quantitatively determining the amount of anti-*Mycoplasma* IgG antibodies and/or the amount of anti-*Mycoplasma* IgM antibodies in said biological fluid.

34. The method of claim 16, wherein said biological fluid is collected from a mammalian subject.

* * * * *

UNITED STATES PATENT AND TRADEMARK OFFICE
CERTIFICATE OF CORRECTION

PATENT NO. : 10,222,383 B2
APPLICATION NO. : 15/418477
DATED : March 5, 2019
INVENTOR(S) : Campbell et al.

Page 1 of 1

It is certified that error appears in the above-identified patent and that said Letters Patent is hereby corrected as shown below:

In the Specification

Column 2, Line 31: Please correct "and detecting" to read -- and (f) detecting --

Column 15, Line 33: Please correct "2'" to read -- 2$^{nd}$ --

Column 18, Line 17: Please correct "Specim,en" to read -- Specimen --

Signed and Sealed this
Twenty-fifth Day of June, 2019

Andrei Iancu
*Director of the United States Patent and Trademark Office*